United States Patent
Souza et al.

(10) Patent No.: US 7,323,576 B2
(45) Date of Patent: Jan. 29, 2008

(54) SYNTHETIC ROUTE TO DRONABINOL

(75) Inventors: Fabio E. S. Souza, Mississauga (CA); Jason E. Field, Mississauga (CA); Ming Pan, Mississauga (CA); Navindra J. Ramjit, Mississauga (CA); Tharsika Tharmanathan, Markham (CA); Tracey Jende-Tindall, Aurora (CA)

(73) Assignee: Alphora Research Inc., Mississauga, Ontario (CA)

( * ) Notice: Subject to any disclaimer, the term of this patent is extended or adjusted under 35 U.S.C. 154(b) by 376 days.

(21) Appl. No.: 10/954,345

(22) Filed: Oct. 1, 2004

(65) Prior Publication Data

US 2006/0074252 A1    Apr. 6, 2006

(51) Int. Cl.
*C07D 311/80*    (2006.01)
(52) U.S. Cl. .................................................. 549/390
(58) Field of Classification Search ................. 549/390
See application file for complete search history.

(56) References Cited

U.S. PATENT DOCUMENTS

| | | |
|---|---|---|
| 3,656,906 A | 4/1972 | Bullock |
| 3,734,930 A | 5/1973 | Razdan et al. |
| 4,116,979 A | 9/1978 | Razdan et al. |
| 4,381,399 A | 4/1983 | Olsen et al. |
| 5,227,537 A | 7/1993 | Stoss et al. |

FOREIGN PATENT DOCUMENTS

| | | |
|---|---|---|
| WO | WO 02/070506 A2 | 9/2002 |
| WO | WO 02/096899 A1 | 12/2002 |

OTHER PUBLICATIONS

Vaultier et. al., 1987; vol. 28, No. 36; pp. 4169-4172 "Tetrahedron Letters", Great Britain.

Anglea et. al., 1987; vol. 43, No. 23; pp. 5537-5543 "Tetrahedron", Great Britain.

Handrick et. al., 1979; No. 8; pp. 681-684 "Tetrahedron Letters", Great Britain.

Banks et. al., 1981; vol. 1; pp. 1096-1102 "J. Chem. Soc., Perkin Trans", Scotland.

Parsons et .al; 1980; pp. 197-198 "J. Chem. Soc., Chem. Commun.", Southampton.

Walter R. Benn, 1968; vol. 33, No. 8; pp. 3113-3118 "Steroidal C-17 Allene Acetates", Chicago, Illinois.

Snider, B. B. and Amin, S. G., 1978; vol. 8; pp. 117-125 "Synthetic Communication", New Jersey.

Garrett et. al., 1978; vol. 67, No. 1; pp. 27-32 "Journal of Pharmaceutical Sciences", The Netherlands.

Synlett, 1991; pp. 553-554 by Stoss et al, "A Useful Approach Towards $\Delta^9$-Tetrahydrocannabinol", Germany.

"Helvetica Chimica Acta", 1988; vol. 71; pp. 209-217 Zurich by Burkard et al.

Schlossarczyk et. al, 1973; vol. 56, No. 3; pp. 875-944 "Helvetica Chimica Acta", Zurich.

Evans et. al, 1999; vol. 121; pp. 7582-7594 "Journal of the American Chemical Society", Massachusetts.

"Izveshya Akademii Nauk SSSR, Seriya Khimicheskaya", 1979; No. 5; pp. 1049-1052. by Arbuzov et al.

*Primary Examiner*—Taofiq Solola
(74) *Attorney, Agent, or Firm*—Robert G. Hirons

(57) ABSTRACT

Dronabinol, the tetrahydrocannabinol compound which comprises the active constituent of marijuana and is pharmaceutically useful as an antiemetic, is prepared by a process involving reaction of cis-menth-1-ene-3,8-diol with olivetol to form 1,3-dihydroxy-2-[(1R,6R)-6-(2-hydroxyprop-2-yl)-3-methylcyclohex-2-en-1-yl]-5-pentylbenzene; and cyclizing the 1,3-dihydroxy-2-[(1R,6R)-6-(2-hydroxyprop-2-yl)-3-methylcyclohex-2-en-1-yl]-5-pentylbenzene so formed to obtain dronabinol. A novel synthesis of cis-menth-1-ene-3,8-diol is also provided.

9 Claims, 2 Drawing Sheets

SYNTHETIC ROUTE TO DRONABINOL

FIELD OF THE INVENTION

Figure 1:
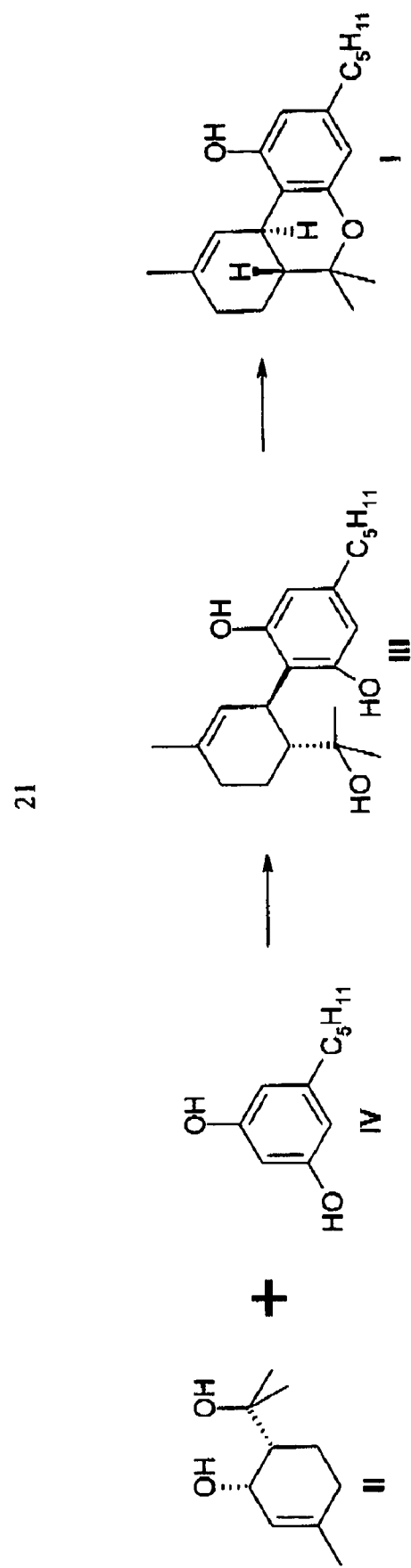

This invention relates to organic chemical synthesis and compounds useful therein. More specifically, it relates to processes for synthesizing the class of pharmaceutically active products known as tetrahydrocannabinols, as exemplified by dronabinol, and to chemical compounds useful as intermediates in such processes.

BACKGROUND OF THE INVENTION

Tetrahydrocannabinols are the active constituents of marijuana (hashish). The major active form, the $\Delta^1$-3,4-trans isomer of chemical formula:

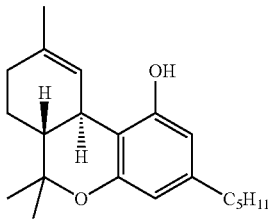

I known as $\Delta^9$-THC, or by the generic name dronabinol, has approved pharmaceutical applications as an anti-emetic, e.g. for enhancing appetite in patients suffering side effects of chemotherapy, suffering from AIDS or anorexia. Its synthesis on a commercial scale presents particular difficulties, however, because the compound possesses several stereoisomeric forms, only one of which, the $\Delta^1$-3,4-trans isomer (dronabinol), is significantly active. Synthetic processes which lead to the production of a mixture of stereoisomers require a step of separation of the stereoisomers, which is difficult and tedious and tends to render such a process economically unattractive. Extraction of dronabinol from its natural plant source presents similar difficulties, since other stereoisomers are naturally present.

BRIEF REFERENCE TO THE PRIOR ART

Handrick et al., *Tetrahedron Letters* 1979, pages 681-684 report a synthetic process for dronabinol which starts from a readily available monoterpene, namely p-menth-2-ene-1,8-diol, of formula:

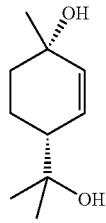

This is reacted with olivetol, 1,3-dihydroxy-5-pentylbenzene, to produce compounds with the desired dibenzopyran ring structure of dronabinol, but along with substantial amounts of other products that then require to be separated.

Evans et al., Journal of the American chemical Society, 1999, volume 121, pages 7582-7594, report a total synthesis of ent-$\Delta^1$-tetrahydrocannabinol, the enantiomer of dronabinol. The process involves a step of coupling olivetol to the allylic alcohol 1-methyl-3-hydroxy-4-(2-hydroxyprop-2-yl)cyclohex-1-ene in which the substituents at the 3-and 4-positions of the cyclohexene ring are in the trans configuration. The resulting coupled product is cyclized and reportedly produces the unnatural enantiomer of dronabinol.

U.S. Pat. No. 5,227,537 Stoss describes a process of reacting cis-p-menth-2-ene-1,8-diol with olivetol to prepare 6,12-dihydro-6-hydroxycannabidiol (alternative nomenclature 1,3-dihydroxy-2-[6-(2-hydroxyprop-2-yl)-3-methylcyclohex-2-en-1-yl]-5-pentylbenzene), followed by cyclization thereof to trans-$\Delta^9$tetrahydrocannabinol. The intermediate 6,12-dihydro-6-hydroxycannabidiol is reportedly readily purified by crystallization.

SUMMARY OF THE INVENTION

It has now been discovered that dronabinol can be prepared, in relatively high yield and high stereoselectivity, by reaction of a cis-configured cyclohexene diol, namely cis-(1S,6R)-6-(2-hydroxyprop-2-yl)-3-methylcyclohex-2-en-1-ol of formula II:

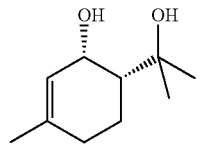

II (hereinafter sometimes cis-menth-1-ene-3,8-diol), with olivetol to produce the appropriate aryl substituted cyclohexene which has the trans configuration of the hydroxyisopropyl and aryl substituents on the cyclohexene ring required for dronabinol. The desired trans compound is crystalline, and so it can be readily purified by recrystallization. The simple cyclization of this trans-configured intermediate, which has the formula:

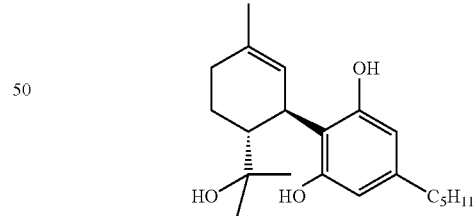

to form the dibenzopyran ring structure of dronabinol retains the stereochemistry of the intermediate, and produces dronabinol in high purity and in good, commercially acceptable yields.

Cis-menth-1-ene-3,8-diol is a known compound—see for example Tetrahedron 1987, 43, pages 5537-5543.

Thus according to the present invention, from one aspect, there is provided a process for preparing 1,3-dihydroxy-2-[(1R,6R)-6-(2-hydroxyprop-2-yl)-3-methylcyclohex-2-en-1-yl]-5-pentylbenzene, of chemical formula:

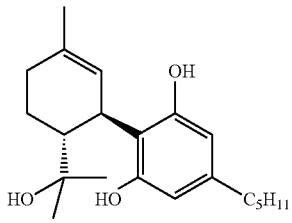

the hydroxyisopropyl group at position 5 and the aryl group at position 6 of the cyclohexene ring being disposed trans to one another, which comprises reacting cis-(1S,6R)-6-(2-hydroxyprop-2-yl)-3-methylcyclohex-2-en-1-ol of formula:

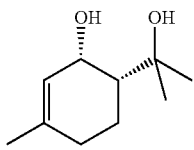

II (the hydroxy and the hydroxyisopropyl substituents being disposed cis to one another), with olivetol (1,3-dihydroxy-5-n-pentylbenzene), of formula:

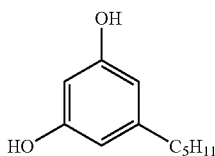

IV

BRIEF REFERENCE TO THE DRAWINGS

Figure 2:
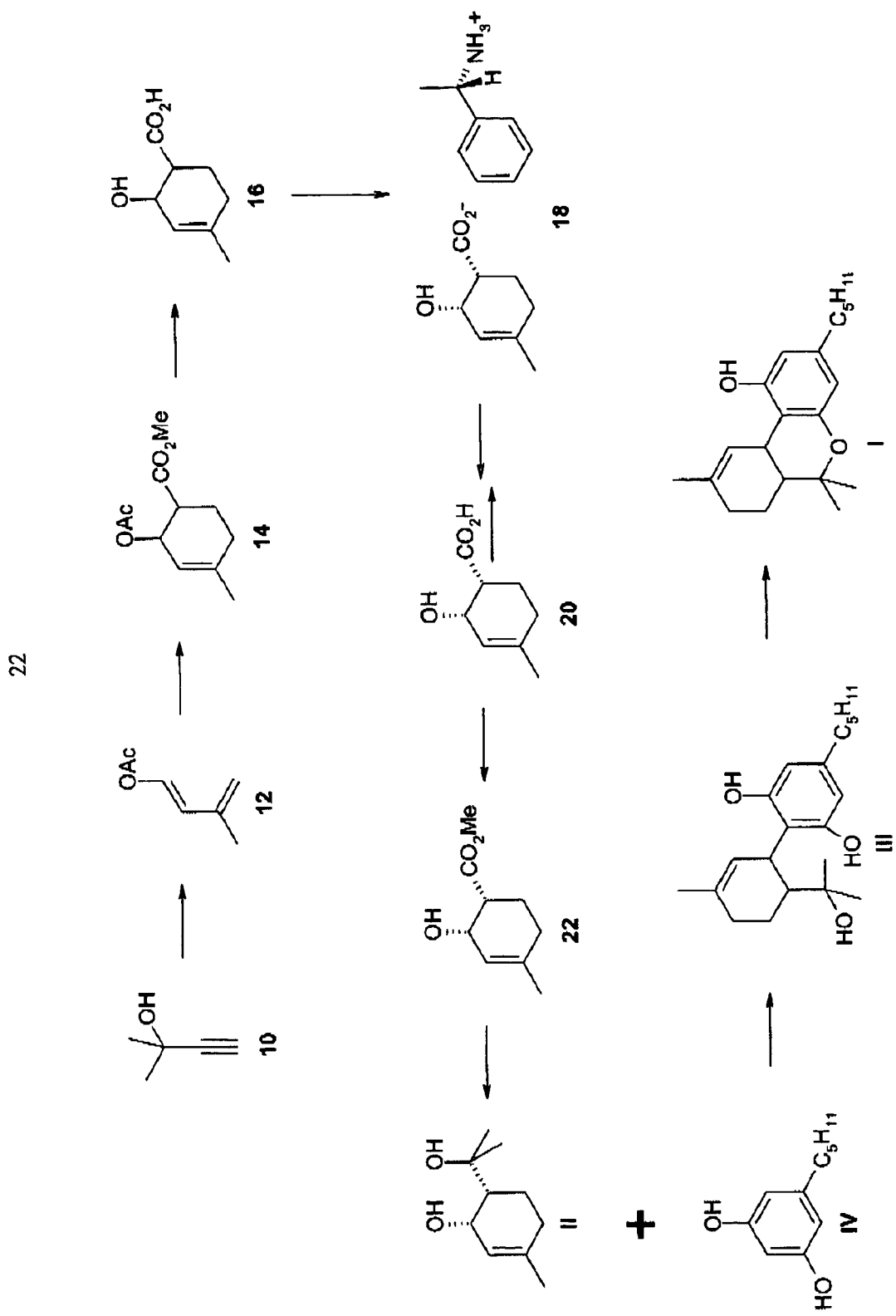

FIG. 1 of the accompanying drawings depicts the chemical reactions of the final two steps of the preferred process of the present invention for preparing dronabinol;

FIG. 2 of the accompanying drawings depicts the preferred overall chemical synthesis according to the present invention, and illustrates novel intermediates.

DESCRIPTION OF THE PREFERRED EMBODIMENTS

The reaction of cis-(1S,6R)-6-(2-hydroxyprop-2-yl)-3-methylcyclohex-2-en-1-ol (II) with olivetol (IV) is conducted using reagents and conditions which have been previously used with analogous starting materials—see for example the aforementioned paper by Handrick et al. The reaction can be conducted in solution in an organic solvent, e.g. methylene chloride, benzene, diethyl ether, and in the presence of the Lewis acid catalyst such as boron trifluoride, zinc chloride, zinc bromide or stannic chloride. A chiral catalyst is not required, to obtain the desired stereoisomers, thereby avoiding significant costs associated with some prior art processes. The reaction takes place over a period of 2-8 hours, at room temperature, preferably with dropwise addition of cis-menth-1-ene-3,8-diol. The resulting trans-configured intermediate (III) can be recovered in relatively pure form by crystallization, and then cyclized to form dronabinol in a subsequent step. Alternatively, the cyclization process can be conducted on the reaction product mixture from the coupling step, without recovering and isolating compound (II), to produce pure dronabinol, essentially free of other stereoisomers. This step of cyclization is known in the art, and can be conducted by known procedures—see for example the aforementioned paper by Evans et al. It may be conducted in solution in any of the previously mentioned solvents, in the presence of a Lewis acid such as zinc chloride or zinc bromide.

These processes are illustrated in accompanying FIG. 1 of the drawings. Cis-menth-1-ene-3,8-diol (compound II) is reacted with olivetol (compound IV) under conditions as described above, resulting in the formation of intermediate (III), which has the trans configuration, in contrast with the cis configuration of compound (II). It is believed that this trans configuration is assumed to minimize steric interactions between substituents on the cyclohexene ring as arylation of compound (II) takes place. The resulting intermediate III is then cyclized to dronabinol (I), maintaining the trans configuration of the intermediate.

From another aspect, the present invention in its preferred embodiment provides a novel process for preparing enantiomerically enriched cis-menth-1-ene-3,8-diol (compound II), in a stereospecific manner. Whilst as noted cis-menth-1-ene-3,8-diol is a known compound, it is not easily available in significantly enantiomerically enriched form, in contrast with the corresponding trans isomer (isolatable according to the procedure described by Evans et. al. in the aforementioned paper). The process of the preferred embodiment of the invention involves several steps, and produces several novel chemical compounds as intermediates in the synthesis. Each of these novel intermediates constitutes a further aspect of the preferred embodiments of this invention.

The starting materials for the overall process are 2-methyl-3-butyn-2-ol (FIG. 2, compound 10), which is commercially available. This is converted to 1-acetoxy-3-methyl-1,3-butadiene (compound 12), by reaction with acetic anhydride under strongly acidic conditions, e.g. in the presence of phosphoric acid, followed by a rearrangement catalyzed by a transition metal ion, e.g. silver(I) or copper (I). Next, the recovered and purified diene 12 is subjected to a Diels-Alder reaction to form a 2-substituted 4-methylcyclohex-3-ene carboxylic ester of general formula:

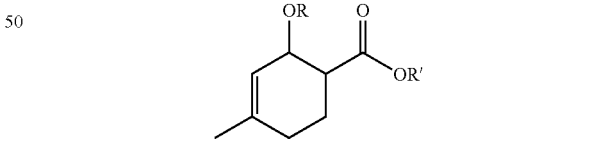

V in which R represents lower ($C_1$-$C_6$) acyl, lower alkyl, silyl, hydrogen, lower alkylsulfonyl, arylsulfonyl, lower alkoxysulfonyl or lower alkoxyphosphoryl, and R' represents hydrogen or lower alkyl. This is a novel class of chemical compounds, constituting a further aspect of the present invention. The class is exemplified by methyl 2-acetoxy-4-methylcyclohex-3-ene carboxylate, compound 14, illustrated on FIG. 2. The Diels-Alder reaction can be accomplished by reaction with methylacrylate in the presence of a polymerization inhibitor such as hydroquinone in solution in inert organic solvent such as toluene or isopropyl acetate, at elevated temperatures. The reaction initially yields a mixture of cis and trans isomers, isolated as a racemate by solvent extraction e.g. with hexane. Upon cooling, e.g. to −20° C., a precipitate is formed, which consists of essentially pure racemic cis isomer. The cis carboxylate 14 is then hydrolyzed with alkali metal hydroxide to yield the free hydroxy acid 16, another novel product, as a racemate. Next, the substituted cyclohexene of formula V as exemplified by 2-hydroxy-4-methylcyclohex-3-ene carboxylic acid 16 is resolved to isolate the desired (1R,2S) enantiomer. This can be achieved using a chiral amine resolving agent, e.g. one of the enantiomers of methylbenzylamine, to form an addition salt of the chiral amine and compound V, such as the benzylamine addition salt illustrated at 18. Such addition salts constitute another class of novel compounds. The salt can be isolated by precipitation, essentially as a single enantiomer. The simple step of basic extraction followed by acidification of an aqueous solution of this chiral salt, e.g. with hydrochloric acid, yields the free hydroxy acid, compound 20, another novel compound, as a single enantiomer, having a cis configuration of the hydroxy and carboxylic acid ring substituents.

Compound 20, (1R,2S)-2-hydroxy-4-methyl cyclohex-3-ene carboxylic acid, in its cis form, is then esterified e.g. by reaction with methanol/acid, methyl iodide or dimethylsulfate, to form the corresponding methyl ester, compound 22. Whilst the methyl ester is the chosen ester, any other lower alkyl or similar ester could be prepared at this stage. The cis configuration is retained. This ester 22 is next converted to cis-(1S,6R)-6-(2-hydroxyprop-2-yl)-3-methylcyclohex-2-en-1-ol, compound II, cis-menth-1-ene-3,8-diol, e.g. by reaction with a methyl magnesium halide at low temperature in solution in tetrahydrofuran.

The process steps of the invention are further described, for illustrative purposes, in the following specific example, a stepwise synthesis of dronabinol according to the preferred embodiment of the invention.

Step 1: Synthesis of 1-acetoxy-3-methyl-1,3-butadiene (12)

A solution of 2-methyl-3-butyn-2-ol (84 g; 1 mol) was added to a stirred solution of phosphoric acid (1.75 g; 0.02 mol) in acetic anhydride (152 g; 1.5 mol) over fifty minutes at room temperature under nitrogen. This reaction is exothermic. To minimize the exothermic of the reaction, the rate of addition of 2-methyl-3-butyn-2-ol was controlled so that the reaction temperature remained in the range of 46° C.-50° C. The solution was stirred at room temperature for 1 hour. TLC showed complete consumption of starting material. The reaction mixture was heated to 70° C. and a slurry of 0.5 g (0.003 mol) of silver carbonate and 3.18 g (0.03 mol) of sodium carbonate in 10 ml of acetic anhydride was added over a period of 30 minutes. The solution was heated at 120° C. for 3½ hours.

Sodium chloride (30 g; 0.5 mol) was then added to the mixture, once it had cooled to 70° C., and heating at 120° C. was continued for 6 hours. The cooled mixture was poured into a mixture of water and tert butyl methyl ether (750 ml each). The organic extract was washed three times with sodium carbonate (200 ml each). The organic extract was dried over a mixture of anhydrous magnesium sulphate and anhydrous potassium carbonate. The solvent was evaporated and the product collected by fractional distillation (60-74° C./36 torr) to give 40.28 g (32%) of 1-acetoxy-3-methyl-1, 3-butadiene.

Step 2: Synthesis of methyl 2-acetoxy-4-methylcyclohex-3-ene carboxylate (14)

A mixture of 1-acetoxy-3-methyl-1-butadiene (15.08 g; 0.12 mol), methyl acrylate (11.2 g; 0.13 mol) and hydroquinone (13 mg; 0.12 mmol)) in toluene (30 ml) was heated for 8 hours at 120° C. The solvent was removed under vacuo. 25 ml of hexane was added into the crude product mixture and the upper layer was decanted and stored in the freezer over night. The resulting crystals were filtered and washed with 10 ml of cold hexane and dried at 20° C. for 3 hours to give 11.65 g (47%) of methyl 2-acetoxy-4-methylcyclohex-3-ene carboxylate.

Step 3: Synthesis of 2-hydroxy-4-methylcyclohex-3-ene carboxylic acid (16)

A 100 mL round-bottom flask equipped with a magnetic stir bar and nitrogen inlet was charged with the acetate ester 14 (5.306 g, 25 mmol) and a solution of LiOH (8.392 g, 200 mmol) in 53 mL of $H_2O$. The reaction was stirred for 3 h at room temperature. TLC (2:1:0.5 Hexane:EtOAc:HOAc) indicated reaction was complete. 20 mL of MTBE was added and the aqueous phase removed to a separate flask. The aqueous solution was cooled to ~5-10° C. and acidified to pH~2 with concentrated HCl. A small amount of precipitate was removed by filtration at room temperature. The filtrate was extracted with 3×40 mL of MTBE and the combined organic layers dried over sodium sulphate and rotovaped to a yellow oil that solidified upon cooling to give 2.798 g (72%) of the hydroxy acid 16.

Step 4: Resolution of 2-hydroxy-4-methylcyclohex-3-ene carboxylic acid

Part A

A 100 mL round-bottom flask equipped with a magnetic stir bar and nitrogen inlet was charged with the hydroxy acid 16 (2.40 g, 15 mmol) and 24 mL of acetone. (+)-methylbenzylamine (1.96 mL, 15 mmol) was added and the white dispersion became clear. After ~0.5 h at room temperature, a white precipitate formed. The reaction was stirred for an additional 1 h at room temperature and the precipitate was collected by vacuum filtration and dried in a vacuum oven to give 1.305 g (31%) of the corresponding chiral salt 18.

Part B

A 200 mL round-bottom flask equipped with a magnetic stir bar, nitrogen inlet, and thermometer was charged with chiral salt (2.795 g, 10 mmol) and 56 mL of saturated aqueous sodium bicarbonate. The solution was stirred to dissolve all solids and then transferred to a separatory funnel and washed with 28 mL of MTBE. The aqueous phase was returned to the flask and cooled to −5° C. 6N HCl was added dropwise until pH=2.00. The temperature did not exceed 0° C. during addition. The solution was transferred to a separatory funnel and the product extracted with 3×28 mL of MTBE. The combined organic phases were washed with brine, dried over sodium sulphate and concentrated to give 1.220 (79%) of the hydroxy acid 20 as a white solid.

Step 5: Synthesis of methyl 2-hydroxy-4-methylcyclohex-3-ene carboxylate (22)

A 100 mL round-bottom flask equipped with a magnetic stir bar and nitrogen inlet was charged with the hydroxy acid (0.781 g, 5 mmol), potassium carbonate (1.037 g, 7.5 mmol)

and 20 mL of acetone. Dimethyl sulphate (0.52 mL, 5.5 mmol) was added and the reaction was stirred at room temperature for 48 h. The reaction was filtered and concentrated to a clear oil. The crude product was purified by flash column chromatography (1:1 hexane:ethylacetate) to yield 0.797 g (92%) of pure hydroxy ester 22 as a clear oil. This product stays as a clear oil until placed under vacuum, at which point fine, needle-like crystals form at the top of the flask (possible sublimation). Seeding the remaining oil with one of these crystals gives the product as a white crystalline solid.

Step 6: Synthesis of 6-(1-Hydroxy-1-methylethyl)-3-methylcyclohex-2-en-1-ol (II)

A 100 mL round-bottom flask equipped with a magnetic stir bar and nitrogen inlet was charged with the hydroxy ester 22 (0.797 g, 4.7 mmol) and 20 mL of THF and then cooled to −78° C. Methylmagnesium bromide (7.80 mL, 23.4 mmol) was added dropwise and the reaction was allowed to warm to room temperature. After stirring at room temperature for 3 h, the reaction was quenched with 10 mL of saturated ammonium chloride. The product was extracted with 2×20 mL of ethyl acetate and the combined organic layers were then dried over sodium sulphate and concentrated to give 0.763 g (95%) of the diol II as a pale yellow oil.

Step 7: Synthesis of 1,3-Dihydroxy-2-[6(1-hydroxy-1-methylethyl)-3-methylcyclohex-2-en-1-yl]-5-pentylbenzene (III)

A 2000 mL round-bottom flask equipped with a magnetic stir bar and nitrogen inlet was charged with dichloromethane (600 mL), olivetol (20.00 g, 111 mmol) and 2.60 g of Camphorsulfonic acid. A solution of diol (20.00 g, 118 mmol) in dichloromethane (600 mL) was added dropwise over a period of 3 hours, and stirring was continued for another 3 h. The reaction was quenched by pouring into 700 mL of saturated sodium bicarbonate, the layers were separated and the aqueous phase was extracted with 2×200 mL of dichloromethane. The combined organic layers were then dried over magnesium sulphate, filtered and concentrated under vacuum to give a brown oil. Crystallization from hexane gives 14.3 g (39%) of the intermediate III as a white solid.

Step 8: Synthesis of Dronabinol (I)

A 1000 mL round-bottom flask equipped with a magnetic stir bar, reflux condenser and nitrogen inlet was charged with dichloromethane (200 mL), zinc chloride (5.30 g, 39 mmol) and magnesium sulfate (28.30 g, 235 mmol). The solvent was brought to reflux, and a solution of intermediate II (13.00 g, 39 mmol) in dichloromethane (200 mL) was added in one portion. The resulting suspension was refluxed for 50 minutes, after which the reaction mixture was quickly cooled in an ice-water bath and then quenched by pouring into 400 mL of saturated sodium bicarbonate. The layers were separated and the aqueous phase was extracted with 2×200 mL of dichloromethane. The combined organic layers were washed once with brine, then dried over magnesium sulfate, filtered and concentrated under vacuum to give a yellow oil. Purification by column chromatography (1:100 ethyl acetate:hexane) gave 6.00 g (49%) of dronabinol as a colorless oil.

REFERENCES

1) Snider, B. B; Amin, S. G. *Synth. Commun.* 1978, 8, 117.
2) Banks et al. *J. Chem. Soc., Perkin Trans.* 1 1981, 1096-1102
3) Benn, W. R. *J. Org. Chem.* 1968, 33, 3113.
4) Parsons et al. *J. Chem. Soc., Chem. Commun.* 1980, 197.
5) Schlossarczyk et al. *Helv. Chem. Acta* 1973, 56, 875.

What is claimed is:

1. A process for preparing 1,3-dihydroxy-1-[1R,6R)-6-(2-hydroxyprop-2-yl)-3-methylcyclohex-2-en-1-yl]-5-pentylbenzene, of chemical formula:

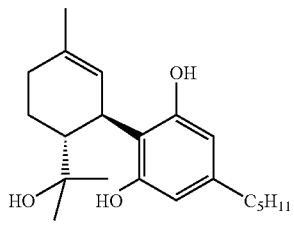

the 2-hydroxyprop-2-yl group at position 6 and the 1,3-dihydroxy-5-pentylphenyl group at position 1 of the cyclohexene ring being disposed trans to one another, which comprises esterifying cis-(1R,2S)-2-hydroxy-4-methylcyclohex-3-ene carboxylic acid to form a lower alkyl ester thereof: subjecting the lower alkyl ester so formed to a nucleophilic addition reaction with an appropriate organometallic compound to form cis-(3S,4R)-1-methyl-3-hydroxy-4-(2-hydroxyprop-2-yl)cyclohex-1-ene of formula:

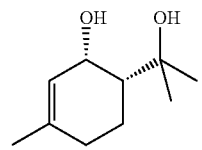

(the hydroxyl and the 2-hydroxyisopropyl substituents being disposed cis to one another), and reacting the cis-(3S,4R)-1-methyl-3-hydroxy-4-(2-hydroxyprop-2-yl)cyclohex-1-ene with olivetol (1,3-dihydroxy-5-n-pentylbenzene), of formula:

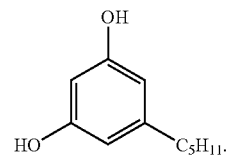

2. The process of claim 1 including the subsequent step of cyclizing the 1,3-dihydroxy-2-[(1R, 6R)-6-(2-hydroxyprop-2-yl)-3-methylcyclohex-2-en-1-yl]-5-pentylbenzene (III) so produced, to form dronabinol of formula:

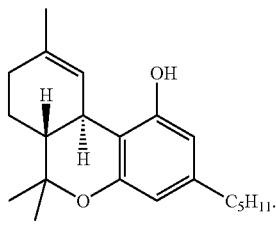

3. The process of claim 1 wherein the organometallic compound is a methyl magnesium halide.

4. The process of claim 1 wherein the lower alkyl ester is a methyl ester.

5. The process of claim 1 including the preceding steps of preparing the cis-2-hydroxy-4-methylcyclohex-3-ene carboxylic acid by subjecting 1-acetoxy-3-methyl-1, 3-butadiene to a Diels-Alder reaction with methyl acrylate, to form racemic methyl 2-acetoxy-4-methyl-cyclohex-3-ene carboxylate, isolating the cis-isomer by crystallization, converting this cis-carboxylate to 2-hydroxy-4-methylcyclohex-3-ene carboxylic acid, and resolving the racemic mixture to obtain cis-(1R,2S)-2-hydroxy-4-methylcyclohex-3-ene carboxylic acid.

6. The process of claim 5 wherein resolution of the racemic mixture is accomplished by forming an amine addition salt with a chiral amine and separately precipitating the (1R,2S) isomer therefrom, followed by re-formation of the free acid.

7. The process of claim 6 wherein the chiral amine is 1-phenylethylamine.

8. The process of claim 5 wherein the 1-acetoxy-3-methyl-1,3-butadiene is prepared by reacting 2-methyl-3-butyn-2-ol with acetic anhydride under acidic conditions, followed by a transition metal ion catalyzed molecular rearrangement.

9. A process of preparing dronabinol, of formula:

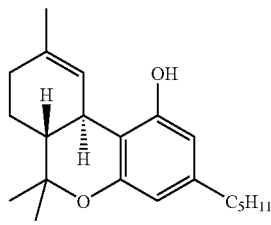

which comprises the successive steps of:
(a) reacting 2-methyl-3-butyn-2-ol with acetic anhydride under acidic conditions, followed by transition metal catalyzed rearrangement, to obtain 1-acetoxy-3-methyl-1,3-butadiene;
(b) subjecting the 1-acetoxy-3-methyl-1,3-butadiene so obtained to Diels-Alder reaction with methyl acrylate to form methyl 2-acetoxy-4-methyl cyclohex-3-ene carboxylate;
(c) isolating the racemic cis isomer of methyl 2-acetoxy-4-methyl cyclohex-3-ene carboxylate by crystallization;
(d) converting this carboxylate to racemic cis-2-hydroxy-4-methylcyclohex-3-ene carboxylic acid;
(e) resolving the racemic mixture to obtain significantly enantiomerically enriched cis-2-hydroxy-4-methylcyclohex-3-ene carboxylic acid;
(f) esterifying the resolved cis-2-hydroxy-4-methylcyclohex-3-ene carboxylic acid to form a lower alkyl ester thereof
(g) reacting the lower alkyl ester so formed with a methyl magnesium halide to form cis-menth-1-ene-3,8-diol;
(h) reacting cis-menth-1-ene-3,8-diol with olivetol to form 1,3-dihydroxy-2-[(1R,6R)-6-(2-hydroxyprop-2-yl)-3-methylcyclohex-2-en-1-yl]-5-n-pentylbenzene; and
(i) cyclizing the 1,3-dihydroxy-2-[(1R,6R)-6-(2-hydroxyprop-2-yl)-3-methylcyclohex-2-en-1-yl]-5-n-pentylbenzene so formed to obtain dronabinol.

* * * * *